US010052767B2

(12) United States Patent
Maruyama et al.

(10) Patent No.: US 10,052,767 B2
(45) Date of Patent: Aug. 21, 2018

(54) ROBOT, CONTROL DEVICE, AND CONTROL METHOD

(71) Applicant: Seiko Epson Corporation, Tokyo (JP)

(72) Inventors: Kenichi Maruyama, Tatsuno (JP); Takashi Nammoto, Azumino (JP); Tomoki Harada, Matsumoto (JP)

(73) Assignee: Seiko Epson Corporation (JP)

( * ) Notice: Subject to any disclaimer, the term of this patent is extended or adjusted under 35 U.S.C. 154(b) by 58 days.

(21) Appl. No.: 15/183,978

(22) Filed: Jun. 16, 2016

(65) Prior Publication Data

US 2016/0368150 A1    Dec. 22, 2016

(30) Foreign Application Priority Data

Jun. 17, 2015  (JP) ................................ 2015-121782

(51) Int. Cl.
| | | |
|---|---|---|
| *B25J 9/16* | (2006.01) | |
| *B25J 19/02* | (2006.01) | |
| *B25J 21/00* | (2006.01) | |
| *G07F 11/16* | (2006.01) | |
| *G07F 11/62* | (2006.01) | |
| *G05B 19/418* | (2006.01) | |
| *G01N 35/00* | (2006.01) | |
| *G01N 21/90* | (2006.01) | |

(52) U.S. Cl.
CPC .......... *B25J 9/1697* (2013.01); *B25J 9/1661* (2013.01); *B25J 9/1664* (2013.01); *B25J 19/021* (2013.01); *B25J 21/00* (2013.01); *G01N 21/9081* (2013.01); *G01N 35/0099* (2013.01); *G05B 19/41815* (2013.01); *G07F 11/165* (2013.01); *G07F 11/62* (2013.01)

(58) Field of Classification Search
CPC .......... G07F 11/165; G07F 11/62; G07F 9/10; G01N 35/0099; G01N 21/9081; G05B 19/41815; G05B 2219/31075; G06T 1/0014; B25J 9/1697; B25J 21/00; B25J 19/021; B25J 9/1661; B25J 9/1664
See application file for complete search history.

(56) References Cited

U.S. PATENT DOCUMENTS

| | | | | |
|---|---|---|---|---|
| 6,045,755 A * | 4/2000 | Lebl | ........................... | B01J 3/03 422/131 |
| 7,313,464 B1 * | 12/2007 | Perreault | ................ | B25J 9/1666 318/568.1 |
| 7,783,383 B2 * | 8/2010 | Eliuk | ........................ | A61J 1/20 141/1 |
| 2001/0022109 A1 * | 9/2001 | Wenninger | ........... | B25J 19/0075 74/18 |
| 2002/0039183 A1 * | 4/2002 | Yagita | ................ | G01N 21/9027 356/240.1 |

(Continued)

FOREIGN PATENT DOCUMENTS

| | | |
|---|---|---|
| JP | 2003-344044 A | 12/2003 |
| JP | 2006-082171 A | 3/2006 |
| WO | WO-2014-054183 A1 | 4/2014 |

*Primary Examiner* — Jason Holloway

(74) *Attorney, Agent, or Firm* — Harness, Dickey & Pierce, P.L.C.

(57) ABSTRACT

A robot, wherein the robot operates on the basis of a picked-up image of at least a part of a work space of the robot picked up by an image pickup section, and a transparent member is disposed between the robot and the work space of the robot.

9 Claims, 9 Drawing Sheets

(56) References Cited

U.S. PATENT DOCUMENTS

| | | | | |
|---|---|---|---|---|
| 2006/0259195 A1* | 11/2006 | Eliuk | A61J 1/20 | 700/245 |
| 2010/0063629 A1* | 3/2010 | Battisti | B25J 9/1679 | 700/259 |
| 2010/0275636 A1* | 11/2010 | Yoshimura | A01N 1/0257 | 62/374 |
| 2010/0291669 A1* | 11/2010 | Robinson | G01N 35/0099 | 435/287.3 |
| 2013/0086801 A1* | 4/2013 | Mimura | B23P 21/00 | 29/720 |
| 2014/0072998 A1* | 3/2014 | Ronsick | G01N 35/0099 | 435/30 |
| 2014/0277713 A1* | 9/2014 | Kouno | B25J 9/0084 | 700/248 |
| 2015/0210410 A1* | 7/2015 | Umeno | A61J 1/2096 | 53/51 |

* cited by examiner

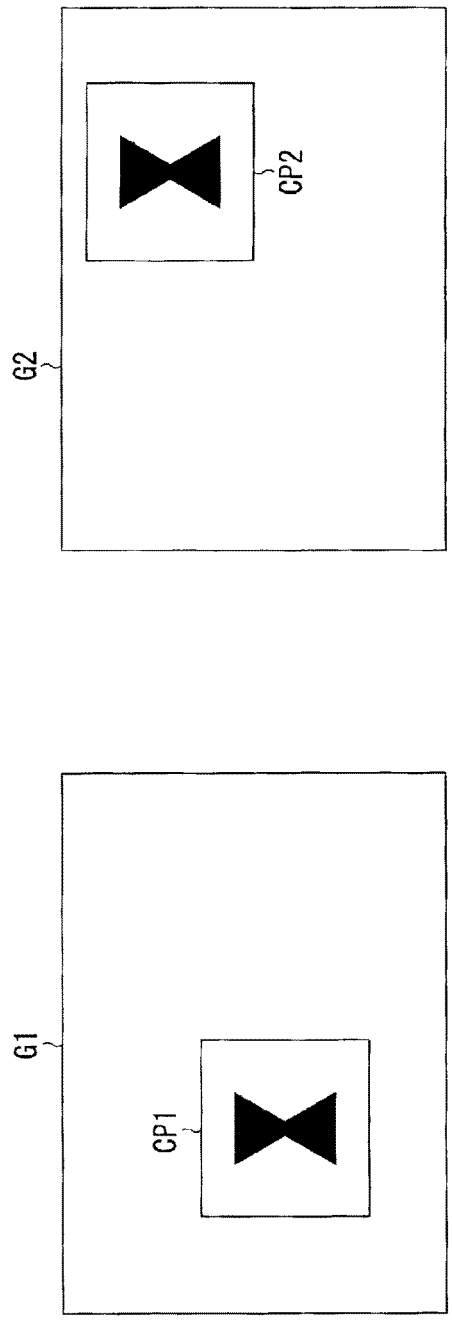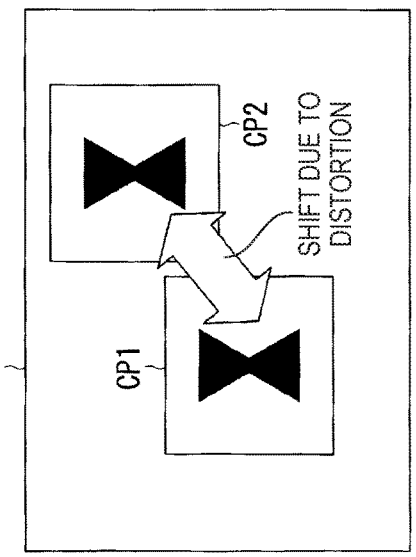
FIG. 7A
FIG. 7B
FIG. 7C

ROBOT, CONTROL DEVICE, AND CONTROL METHOD

BACKGROUND

1. Technical Field

The present invention relates to a robot, a control device, and a control method.

2. Related Art

Researches and developments of a robot that picks up an image of an object with an image pickup section and performs predetermined work on the object on the basis of the picked-up image have been conducted.

In this relation, there has been known a robot that performs predetermined work on an object disposed in a work space in a safe cabinet (see WO2014/054183 (Patent Literature 1)).

However, in the robot of the related art, information indicating the position and the posture of the object in the work space is stored in advance. It is necessary to store (teach) the position and the posture of the object again every time the position and the posture of the object are changed. When the position and the posture of the object in the work space shift because of some reason, it is difficult for the robot to accurately perform the predetermined work. As a result, in the robot, it is sometimes difficult to improve efficiency and accuracy of work in the work space in the safe cabinet.

SUMMARY

An aspect of the invention is directed to a robot which operates on the basis of a picked-up image of at least apart of a work space of the robot picked up by an image pickup section, in which a transparent member is disposed between the robot and the work space of the robot.

With this configuration, in the robot, the transparent member is disposed between the robot and the work space of the robot, and the robot operates on the basis of the picked-up image of at least a part of the work space of the robot picked up by the image pickup section. Consequently, the robot can improve efficiency and accuracy of work. For example, the robot can improve efficiency and accuracy of work in a work space surrounded by a transparent member such as a clean bench.

In another aspect of the invention, the robot may include the image pickup section.

With this configuration, the robot operates on the basis of a picked-up image picked up by the image pickup section included in the robot. Consequently, the robot can improve efficiency and accuracy of work using the image pickup section included in the robot.

In another aspect of the invention, the robot may move the image pickup section into the work space and pick up an image of at least a part of the work space.

With this configuration, the robot picks up an image of at least a part of the work space with the image pickup section moved into the work space. Consequently, the robot can move the image pickup section into the work space and improve efficiency and accuracy of work.

In another aspect of the invention, the robot may operate on the basis of the picked-up image obtained by picking up an image of at least a part of the work space with the image pickup section via the transparent member and a reference image.

With this configuration, the robot operates on the basis of the picked-up image obtained by picking up an image of at least a part of the work space with the image pickup section via the transparent member and the reference image. Consequently, the robot can improve efficiency and accuracy of work using the image pickup section that picks up an image of the work space via the transparent member.

In another aspect of the invention, the picked-up image may be an image including a predetermined image, and the reference image is an image including the predetermined image picked up by the image pickup section not via the transparent member.

With this configuration, the robot operates on the basis of the picked-up image including the predetermined image picked up via the transparent member and the reference image including the predetermined image picked up by the image pickup section not via the transparent member. Consequently, the robot can improve efficiency and accuracy of work on the basis of the picked-up image including the predetermined image and the reference image including the predetermined image.

In another aspect of the invention, the predetermined image may be an image of a marker.

With this configuration, the robot operates on the basis of the picked-up image picked up via the transparent member and including the image of the marker and the reference image picked up by the image pickup section not via the transparent member and including the image of the marker. Consequently, the robot can improve efficiency and accuracy of work on the basis of the picked-up image including the image of the marker and the reference image including the image of the marker.

In another aspect of the invention, the predetermined image may be an image of a part of the robot.

With this configuration, the robot operates on the basis of the picked-up image picked up via the transparent member and including the image of a part of the robot and the reference image picked up by the image pickup section not via the transparent member and including the image of a part of the robot. Consequently, the robot can improve efficiency and accuracy of work on the basis of the picked-up image including the image of a part of the robot and the reference image including the image of a part of the robot.

In another aspect of the invention, the image pickup section may be provided outside the work space.

With this configuration, the robot operates on the basis of a picked-up image picked up by the image pickup section provided outside the work space. Consequently, the robot can improve efficiency and accuracy of work using the image pickup section provided outside the work space.

In another aspect of the invention, the image pickup section may be provided in the work space.

With this configuration, the robot operates on the basis of a picked-up image picked up by the image pickup section provided in the work space. Consequently, the robot can improve efficiency and accuracy of work using the image pickup section provided in the work space.

Still another aspect of the invention is directed to a control device, which causes a robot to operate on the basis of a picked-up image of at least a part of a work space of the robot picked up by an image pickup section, in which a transparent member is disposed between the robot and the work space of the robot.

With this configuration, the transparent member is disposed between the robot and the work space of the robot, and the control device causes the robot to operate on the basis of the picked-up image of at least a part of the work space of the robot picked up by the image pickup section. Consequently, the control device can improve efficiency and accuracy of work.

Yet another aspect of the invention is directed to a control method, which causes a robot to operate on the basis of a picked-up image of at least a part of a work space of the robot picked up by an image pickup section, in which a transparent member is disposed between the robot and the work space of the robot.

With this configuration, the transparent member is disposed between the robot and the work space of the robot, and the control method causes the robot to operate on the basis of the picked-up image of at least a part of the work space of the robot picked up by the image pickup section. Consequently, the control method can improve efficiency and accuracy of work.

As explained above, in the robot, the transparent member is disposed between the robot and the work space of the robot. The robot operates on the basis of the picked-up image of at least a part of the work space of the robot picked up by the image pickup section. Consequently, the robot can improve efficiency and accuracy of work.

In the control device and the control method, the transparent member is disposed between the robot and the work space of the robot. The control device and the control method cause the robot to operate on the basis of the picked-up image of at least a part of the work space of the robot picked up by the image pickup section. Consequently, the control device and the control method can improve efficiency and accuracy of work.

BRIEF DESCRIPTION OF THE DRAWINGS

The invention will be described with reference to the accompanying drawings, wherein like numbers reference like elements.

FIGS. 7A to 7C are diagrams showing an example of a target image in which an image detecting section detects a predetermined image in step S230 and an example of a reference image acquired by an image acquiring section in step S240.

DESCRIPTION OF EXEMPLARY EMBODIMENTS

Embodiment

Figure 1:
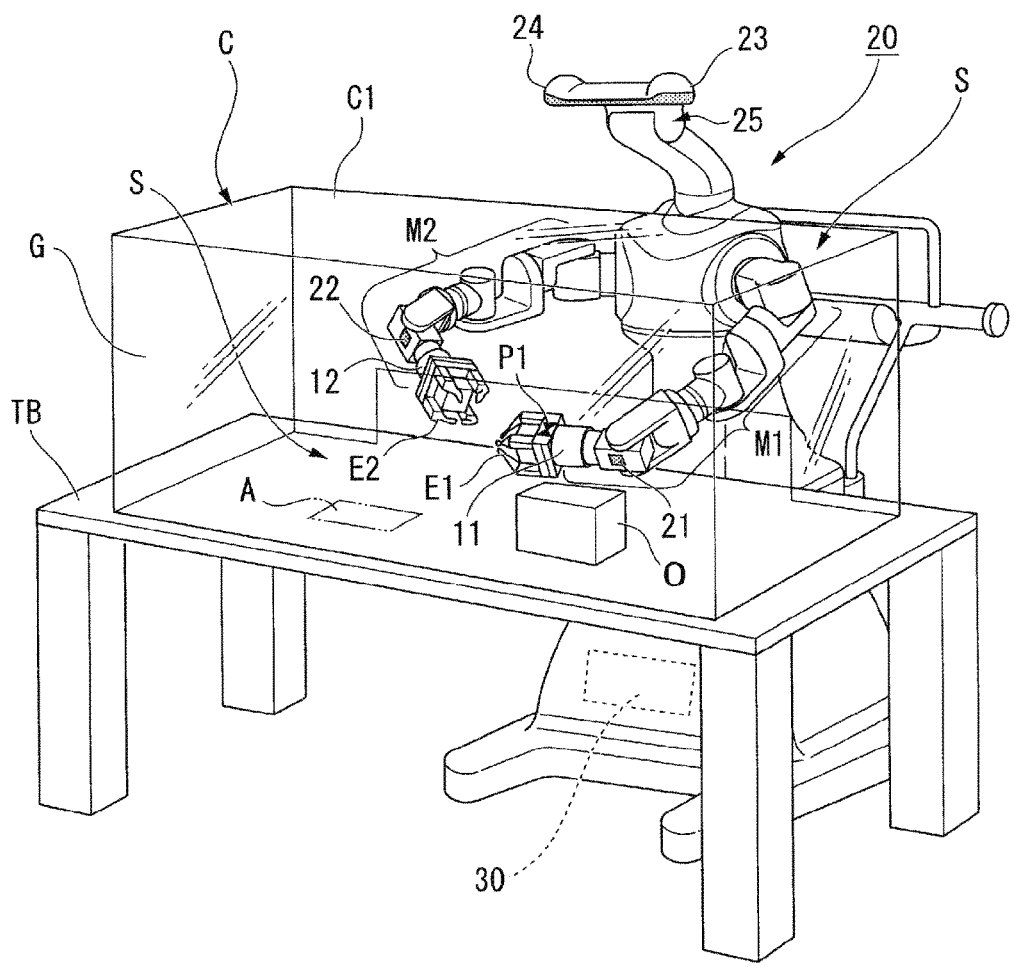
FIG. 1 is a configuration diagram showing an example of a robot according to an embodiment.

An embodiment of the invention is explained below with reference to the drawings. FIG. 1 is a configuration diagram showing an example of a robot 20 according to this embodiment.

First, the configuration of the robot 20 is explained.

The robot 20 is a double-arm robot including a first arm and a second arm. The double-arm robot is a robot including two arms like the first arm and the second arm in this example. Note that the robot 20 may be a single-arm robot instead of the double-arm robot. The single-arm robot is a robot including one arm. For example, the single-arm robot includes one of the first arm and the second arm.

The robot 20 includes a first force sensor 11, a second force sensor 12, a first image pickup section 21, a second image pickup section 22, a third image pickup section 23, a fourth image pickup section 24, a rotating section 25, and a control device 30. Note that the robot 20 may not include one or both of the first force sensor 11 and the second force sensor 12. The robot 20 may not include a part of the first image pickup section 21, the second image pickup section 22, the third image pickup section 23, and the fourth image pickup section 24.

The first arm includes a first end effector E1 including a claw section capable of gripping an object, a first manipulator M1, the first force sensor 11, the first image pickup section 21, and a not-shown plurality of actuators. In the following explanation, the plurality of actuators included in the first arm are collectively referred to as first actuators. The first arm is an arm of a seven-axis vertical multi-joint type. Specifically, the first arm performs an operation of a degree of freedom of seven axes according to an associated operation of a supporting table, the first end effector E1, and the first manipulator M1 by the first actuators. Note that the first arm may be configured to operate at a degree of freedom of six axes or less or may be configured to operate at a degree of freedom of eight axes or more.

When the first arm operates at the degree of freedom of seven axes, the first arm can take more postures compared with when the first arm operates at the degree of freedom of six axes or less. Consequently, for example, the first arm operates smoothly. Further, the first arm can easily avoid interference with an object present around the first arm. When the first arm operates at the degree of freedom of seven axes, control of the first arm can be easily performed with less computational complexity compared with when the first arm operates at the degree of freedom eight axes or more. Because of such reasons, the first arm desirably operates at the degree of freedom of seven axes.

The first actuators are communicably connected to the control device 30 by a cable. Consequently, the first actuators can cause the first end effector E1 and the first manipulator M1 to operate on the basis of a control signal acquired from the control device 30. Note that wired communication via the cable is performed according a standard such as an Ethernet (registered trademark) or a USB (Universal Serial Bus). A part or all of the first actuators may be connected to the control device 30 by radio communication performed according to a communication standard such as Wi-Fi (registered trademark).

The first force sensor 11 is provided between the first end effector E1 and the first manipulator M1. The first force sensor 11 detects a force or a moment acting on the first end effector E1. The first force sensor 11 outputs first force sensor information including, as an output value, a value indicating the magnitude of the detected force or moment to the control device 30 through communication. The first force sensor information is used for control of the first arm based on the first force sensor information by the control device 30. The control based on the first force sensor information refers to, for example, compliance control such as impedance control. Note that the first force sensor 11 may be another sensor such as a torque sensor that detects the magnitude of the force or the moment applied to the first end effector E1.

The first force sensor 11 is communicably connected to the control device 30 by a cable. Wired communication via the cable is performed according to the standard such as the Ethernet (registered trademark) or the USB. Note that the first force sensor 11 may be connected to the control device by radio communication performed according to the communication standard such as the Wi-Fi (registered trademark).

The first image pickup section 21 is a camera including, for example, a CCD (Charge Coupled Device) or a CMOS (Complementary Metal Oxide Semiconductor), which is an image pickup device that converts condensed light into an electric signal. In this example, the first image pickup section 21 is provided in a part of the first manipulator M1. Therefore, the first image pickup section 21 moves according to a movement of the first arm. A range in which image pickup by the first image pickup section 21 is possible changes according to the movement of the first arm. The first image pickup section 21 may pick up a still image of the range or may pick up a moving image of the range. In this example, the first image pickup section 21 picks up a still image of the image pickup possible range.

The first image pickup section 21 is communicably connected to the control device 30 by a cable. Wired communication via the cable is performed according to the standard such as the Ethernet (registered trademark) or the USB. Note that the first image pickup section 21 may be connected to the control device 30 by radio communication performed according to the communication standard such as the Wi-Fi (registered trademark).

The second arm includes a second end effector E2, a second manipulator M2, a second force sensor 12, a second image pickup section 22, and a not-shown plurality of actuators. In the following explanation, the plurality of actuators included in the second arm are collectively referred to as second actuators. The second arm is an arm of a seven-axis vertical multi-joint type. Specifically, the second arm performs an operation of a degree of freedom of seven axes according to an associated operation of the supporting table, the second end effector E2, and the second manipulator M2 by the second actuators. The second arm desirably operates at the degree of freedom of seven axes because of a reason same as the reason why the first arm desirably operates at the degree of freedom of seven axes. Note that the second arm may be configured to operate at a degree of freedom of six axes or less or may be configured to operate at a degree of freedom of eight axes or more.

The second actuators are communicably connected to the control device 30 by a cable. Consequently, the second actuators can cause the second end effector E2 and the second manipulator M2 to operate on the basis of a control signal acquired from the control device 30. Note that wired communication via the cable is performed according to the standard such as the Ethernet (registered trademark) or the USB (Universal Serial Bus). A part or all of the second actuators may be connected to the control device 30 by radio communication performed according to the communication standard such as the Wi-Fi (registered trademark).

The second force sensor 12 is provided between the second end effector E2 and the second manipulator M2. The second force sensor 12 detects a force or a moment acting on the second end effector E2. The second force sensor 12 outputs second force sensor information including, as an output value of the second force sensor 12, a value indicating the magnitude of the detected force or moment to the control device 30 through communication. The second force sensor information is used for control of the second arm based on the second force sensor information by the control device 30. The control based on the second force sensor information refers to, for example, compliance control such as impedance control. Note that the second force sensor 12 may be another sensor such as a torque sensor that detects the magnitude of the force or the moment applied to the second end effector E2.

The second force sensor 12 is communicably connected to the control device 30 by a cable. Wired communication via the cable is performed according to the standard such as the Ethernet (registered trademark) or the USB. Note that the second force sensor 12 may be connected to the control device by radio communication performed according to the communication standard such as the Wi-Fi (registered trademark).

The second image pickup section 22 is a camera including, for example, a CCD or a CMOS, which is an image pickup device that converts condensed light into an electric signal. In this example, the second image pickup section 22 is provided in a part of the second manipulator M2. Therefore, the second image pickup section 22 moves according to a movement of the second arm. A range in which image pickup by the second image pickup section 22 is possible changes according to the movement of the second arm. The second image pickup section 22 may pick up a still image of the range or may pick up a moving image of the range. In this example, the second image pickup section 22 picks up a still image of the image pickup possible range.

The second image pickup section 22 is communicably connected to the control device 30 by a cable. Wired communication via the cable is performed according to the standard such as the Ethernet (registered trademark) or the USB. Note that the second image pickup section 22 may be connected to the control device 30 by radio communication performed according to the communication standard such as the Wi-Fi (registered trademark).

A marker P1 shown in FIG. 1 is provided in one or both of the first arm and the second arm. In this example, the marker P1 is a pattern having a shape obtained by reversing one of two triangles and superimposing the one triangle on the other as shown in FIG. 1. Note that, instead of the pattern shown in FIG. 1, the marker P1 may be another pattern identifiable by the control device 30 or may be a character, a number, a sign, or the like.

When the marker P1 is provided in the first arm, the marker P1 is provided in a position where a part or the entire surface opposite to a surface of the marker P1 in contact with the first arm is not hidden by a part of the first arm. When the marker P1 is provided in the second arm, the marker P1 is provided in a position where a part or the entire surface opposite to a surface of the marker P1 in contact with the second arm is not hidden by a part of the second arm.

In this example, the marker P1 is provided on the surface of the first end effector E1 of the first arm. Note that, when the marker P1 is provided in the first arm, the first image pickup section 21 cannot pick up an image of the marker P1.

Therefore, when an image of the marker P1 is picked up by an image pickup section included in the robot 20, at least any one of the second image pickup section 22, the third image pickup section 23, and the fourth image pickup section 24 has to be provided in the robot 20.

The third image pickup section 23 is a camera including, for example, a CCD or a CMOS, which is an image pickup device that converts condensed light into an electric signal. The third image pickup section 23 is included in the rotating section 25. Therefore, the third image pickup section 23 rotates according to rotation of the rotating section 25. A range in which image pickup by the third image pickup section 23 is possible changes according to the rotation of the rotating section 25. The third image pickup section 23 may pick up a still image in an image pickup space or may pick up a moving image in the image pickup space. In this example, the third image pickup section 23 picks up a still image of the image pickup possible range.

The third image pickup section 23 is communicably connected to the control device 30 by a cable. Wired communication via the cable is performed according to the standard such as the Ethernet (registered trademark) or the USB. Note that the third image pickup section 23 may be connected to the control device 30 by radio communication performed according to the communication standard such as the Wi-Fi (registered trademark).

The fourth image pickup section 24 is a camera including, for example, a CCD or a CMOS, which is an image pickup device that converts condensed light into an electric signal. The fourth image pickup section 24 is included in the rotating section 25 together with the third image pickup section 23. Therefore, the fourth image pickup section 24 rotates according to the rotation of the rotating section 25. The fourth image pickup section 24 is provided in a part where the fourth image pickup section 24 can pick up a stereo image of the image pickup possible range in conjunction with the third image pickup section 23, which is a part of the rotating section 25. That is, a range in which image pickup by the fourth image pickup section 24 is possible changes according to the rotation of the rotating section 25 together with the range in which the image pickup by the third image pickup section 23 is possible. Note that the fourth image pickup section 24 may pick up a still image in an image pickup space or may pick up a moving image in the image pickup space. In this example, the fourth image pickup section 24 picks up a still image of the image pickup possible range.

The fourth image pickup section 24 is communicably connected to the control device 30 by a cable. Wired communication via the cable is performed according to the standard such as the Ethernet (registered trademark) or the USB. Note that the fourth image pickup section 24 may be connected to the control device 30 by radio communication performed according to the communication standard such as the Wi-Fi (registered trademark).

In this example, the functional sections included in the robot 20 explained above acquire control signals from the control device 30 incorporated in the robot 20. The functional sections perform operations based on the acquired control signals. Note that, instead of incorporating the control device 30, the robot 20 may be controlled by the control device 30 set on the outside.

The control device 30 transmits a control signal to the robot 20 to thereby cause the robot 20 to operate. Consequently, the control device 30 causes the robot 20 to perform predetermined work.

Processing performed by the control device 30 in order to cause the robot 20 to operate is explained. Note that, in the following explanation, for convenience of explanation, the first image pickup section 21, the second image pickup section 22, the third image pickup section 23, and the fourth image pickup section 24 are sometimes referred to as four image pickup sections included in the robot 20 and explained.

The control device 30 causes the robot 20 to perform the predetermined work on the basis of picked-up images of a work space, between which and the robot 20 a transparent member is disposed, picked up by the four image pickup sections included in the robot 20 or other image pickup sections separate from the robot 20. When the control device 30 causes the robot 20 to perform the predetermined work on the basis of the picked-up images picked up by the other image pickup sections separate from the robot 20, a part or all of the four image pickup sections do not have to be included in the robot 20.

In this example, when the transparent member is disposed between the work space and the robot 20, this indicates that any one of three conditions explained below is satisfied.

Condition 1) When the first image pickup section 21, the image pickup possible range of which changes according to the movement of the first arm, picks up an image of a range including a work region, the position and the posture of the first arm in which an image of the transparent member is picked up on the front side of the work region are sometimes present in the picked-up image together with the work region.

Condition 2) When the second image pickup section 22, the image pickup possible range of which changes according to the movement of the second arm, picks up an image of the range including the work region, the position and the posture of the second arm in which an image of the transparent member is picked up on the front side of the work region are sometimes present in the picked-up image together with the work region.

Condition 3) When one or both of the third image pickup section 23 and the fourth image pickup section 24, the image pickup possible ranges of which change according to the rotation of the rotating section 25, pick up images of the range including the work region, a rotation angle of the rotating section 25 at which an image of the transparent member is picked up on the front side of the work region is sometimes present in the picked-up images together with the work region.

The transparent member refers to a member, the transmittance of which for transmitting visible light is equal to or larger than a predetermined threshold. The predetermined threshold may be any numerical value as long as, when an image of the work space is picked up by the image pickup section via the transparent member, the threshold is transmittance enough for enabling detection of an object in the work space from the picked-up image. The visible light refers to an electromagnetic wave in a wavelength band of approximately 380 nm to 780 nm. The material of the transparent member is, for example, glass, acrylic, vinyl, or a biological membrane. The transparent member may be an object such as a glass plate or an acrylic plate, the shape of which does not change because of, for example, the influence of the movement of the robot 20, the gravity, and wind or may be an object such as a vinyl sheet, the shape of which changes because of, for example, the influence of the movement of the robot 20, the gravity, and wind.

In the following explanation, the work space, between which and the robot 20 the transparent member is disposed, is a space in a clean bench C shown in FIG. 1. The clean bench C is a container configured to, by performing exhaust via an air filter such as an HEPA (High Efficiency Particulate Air Filter), keep the inside of the work space surrounded by a cover C1 at a negative pressure and prevent a toxic substance and the like caused during work from diffusing to the outside. The cover C1 is formed by a transparent member G and is detachable. The cover C1 can be detached from the clean bench C. Note that the transparent member G in this example is glass.

An opening section is provided in the cover C1. In a state in which the cover C1 is attached to the clean bench C, the robot 20 can cause the first arm and the second arm to enter the inside of the cover C1 from the outer side of the cover C1 through the opening section. Consequently, the robot 20 performs the predetermined work on the inner side of the cover C1 in a state in which the cover C1 is attached to the clean bench C. A work space S shown in FIG. 1 refers to a space on the inner side. Note that the first arm and the second arm of the robot 20 in this example operate at a degree of freedom of seven axes. Therefore, when the robot 20 performs the predetermined work on the inner side of the cover C1, it is possible to suppress interference with the cover C1.

In the work space S, at least a part of the upper surface of a work table TB is included. The predetermined work performed by the robot 20 in the work space S using the first arm and the second arm is work that needs to be performed in an aseptic state such as work for assembling an injector with an injection needle, a syringe, and the like disposed on the work table TB, injecting a drug into the assembled injector, and completing the injector with the drum injected therein or work for injecting a drug into a cell being cultivated in a cultivation container. Such work is often performed in biological work, medical work, and pharmaceutical work.

To simplify explanation, as an example, the predetermined work is work for gripping a target object O disposed on the upper surface of the work table TB and supplying the gripped target object O to a material supply region A set on the upper surface of the work table TB as shown in FIG. 1. The predetermined work is an example. The operation of the robot explained below can also be applied to other kinds of work. Note that the position and the posture in which the target object O is disposed on the upper surface of the work table TB are not determined in advance. The target object O can be set in any posture in any position excluding the material supply region A every time the target object O is disposed. In this example, information indicating the position of the material supply region A is stored in the control device 30 in advance.

The target object O shown in FIG. 1 has a rectangular parallelepiped shape but may have another shape. The predetermined work is not limited to the work that needs to be performed in the aseptic state. The predetermined work may be another kind of work such as work that needs to be performed in a clean room such as painting of an object by a color spray or work executable by the robot 20 in the work space S such as assembly work of industrial components.

In causing the robot 20 to perform such predetermined work, the control device 30 calculates the position and the posture of the target object O on the basis of a picked-up image of a space that is at least apart in the work space S and includes the target object O. The control device 30 causes the robot 20 to operate on the basis of the calculated position and the calculated posture and causes the robot 20 to perform the predetermined work. In the following explanation, for convenience of explanation, the space that is at least a part in the work space S and includes the target object O is referred to as an image pickup space.

In this example, a coordinate indicating a position on a picked-up image and a coordinate indicating a position in a robot coordinate system are associated in advance by calibration. However, when the picked-up image is an image obtained by picking up an image of the image pickup space via the cover C1, distortion due to the presence of the cover C1 occurs in the picked-up image. The distortion occurs because of a difference in a refractive index between the cover C1 and the atmosphere. The position of the target object O on the picked-up image and the position of the target object O on a picked-up image obtained by picking up an image of the image pickup space not via the cover C1 shift because of the distortion.

The coordinate associated with the coordinate indicating the position in the robot coordinate system by the calibration is a coordinate indicating a position on an image pickup image in which distortion due to the presence of the cover C1 does not occur. Therefore, when the picked-up image is the image obtained by picking up an image of the image pickup space via the cover C1, the control device 30 performs correction of the distortion on the image pickup image and associates the position of the target object O on the picked-up image with the position of the target object O on the picked-up image obtained by picking up an image of the image pickup space not via the cover C1. Consequently, the control device 30 can accurately calculate the position and the posture of the target object O on the basis of the picked-up image obtained by picking up an image of the image pickup space and subjected to the correction. In the following explanation, for convenience of explanation, the correction is referred to as first correction.

The control device 30 generates first correction information used for performing the first correction on the basis of a target image and a reference image. In this example, the target image is an image obtained by picking up an image of a space including the marker P1 provided in the first end effector E1 in the work space S of the clean bench C attached with the cover C1. In this example, the reference image is an image obtained by picking up an image of the space including the marker P1 provided in the first end effector E1 in the work space S of the clean bench C attached with the cover C1.

Note that a range in which the target image is picked up coincides with a range in which the reference image is picked up. An image of the marker P1 needs to be included in the target image and the reference image. The position and the posture of the marker P1 (i.e., the position and the posture of the first end effector E1) need to be the same in the target image and the reference image.

The first correction information is information that associates a coordinate indicating a position on the target image and a coordinate indicating a position on the reference image. For example, the first correction information is a correspondence table in which the coordinate indicating the position on the target image and the coordinate indicating the position on the reference image are stored in association with each other. In this case, the control device 30 generates the correspondence table as the first correction information on the basis of the position and the posture of the image of the marker P1 included in the target image and the position and the posture of the image of the marker P1 included in the reference image. The control device 30 stores the generated first correction information.

Note that, when the picked-up image is the image obtained by picking up an image of the image pickup space not via the cover C1, the position of the target object O on the picked-up image coincides with the position of the target object O on the picked-up image obtained by picking up an image of the image pickup space not via the cover C1. Therefore, the control device 30 does not perform the first correction on the image pickup image obtained by picking up an image of the image pickup space.

When the picked-up image is an image obtained by picking up an image of the image pickup space via the cover C1 by a part or all of the four image pickup sections included in the robot 20, as explained above, distortion due to the presence of the cover C1 occurs in the picked-up image. Therefore, in this case, the control device 30 performs the first correction on the picked-up image.

The picked-up image may be an image obtained by picking up an image of the image pickup space not via the cover C1 by one or both of the first image pickup section 21 and the second image pickup section 22 included in the robot 20. In this case, since distortion due to the presence of the cover C1 does not occur in the picked-up image, the control device 30 calculates the position and the posture of the target object O on the basis of the picked-up image. For example, the control device 30 causes one or both of the first arm and the second arm to enter the work space S from the opening section provided in the cover C1 to thereby cause one or both of the first image pickup section 21 and the second image pickup section 22 to pick up an image of the image pickup space not via the cover C1. In this case, since distortion due to the presence of the cover C1 does not occur in the picked-up image, the control device 30 does not perform the first correction on the picked-up image.

The picked-up image may be an image obtained by picking up an image of the image pickup space by the image pickup sections separate from the robot 20. In the following explanation, among the separate image pickup sections, the image pickup section set in a position where image pickup of the image pickup space is possible, which is a position outside the work space S, is referred to as extra-region image pickup section. Among the separate image pickup sections, the image pickup section set in a position where image pickup of the image pickup space is possible, which is a position in the work space S, is referred to as an intra-region image pickup section. When the extra-region image pickup section is set, the extra-region image pickup section is set communicably with the control device 30 by wire or radio. When the intra-region image pickup section is set, the intra-region image pickup section is connected communicably with the control device 30 by wire or radio. Note that, as explained above, when the extra-region image pickup section and the intra-region image pickup section are set, a part or all of the four image pickup sections do not have to be included in the robot 20.

When the extra-region image pickup section picks up an image of the image pickup space, the extra-region image pickup section picks up an image of the image pickup space via the cover C1. In this case, since distortion due to the presence of the cover C1 occurs in the picked-up image, the control device 30 performs the first correction on the picked-up image. The control device 30 calculates the position and the posture of the target object O on the basis of the picked-up image subjected to the first correction.

When the intra-region image pickup section picks up an image of the image pickup space, the intra-region image pickup section picks up an image of the image pickup space not via the cover C1. In this case, since distortion due to the presence of the cover C1 does not occur in the picked-up image, the control device 30 does not perform the first correction on the picked-up image. The control device 30 calculates the position and the posture of the target object O on the basis of the picked-up image.

In the following explanation, a method of processing is explained in detail in which the control device 30 calculates the position and the posture of the target object O disposed in the work space S on the basis of the picked-up image subjected to the first correction and the picked-up image not subjected to the first correction and causes the robot 20 to perform the predetermined work.

Note that the first correction is correction different from correction of distortion of a picked-up image caused by aberration of lenses included in the image pickup sections. In the following explanation, the correction of the distortion of the picked-up image caused by the aberration of the lenses included in the image pickup sections is referred to as second correction. The distortion of the picked-up image caused by the aberration of the lenses included in the image pickup sections occurs in both of the picked-up image subjected to the first correction and the picked-up image not subjected to the first correction. Therefore, the control device 30 performs the second correction on both of the picked-up image subjected to the first correction and the picked-up image not subjected to the first correction. In performing the second correction, the control device 30 generates, in advance, second correction information for performing the second correction. The control device 30 stores the generated second correction information. The control device 30 performs the second correction on the picked-up image using the second correction information.

The second correction information is information that associates a coordinate indicating a position on the picked-up image in which distortion occurs because of the aberration of the lenses included in the image pickup sections and a coordinate indicating a position on the picked-up image in which the distortion does not occur. For example, the second correction information is a correspondence table that stores the coordinate indicating the position on the picked-up image in which the distortion occurs because of the aberration of the lenses included in the image pickup sections and the coordinate indicating the position on the picked-up image in which the distortion does not occur in association with each other.

Figure 2:
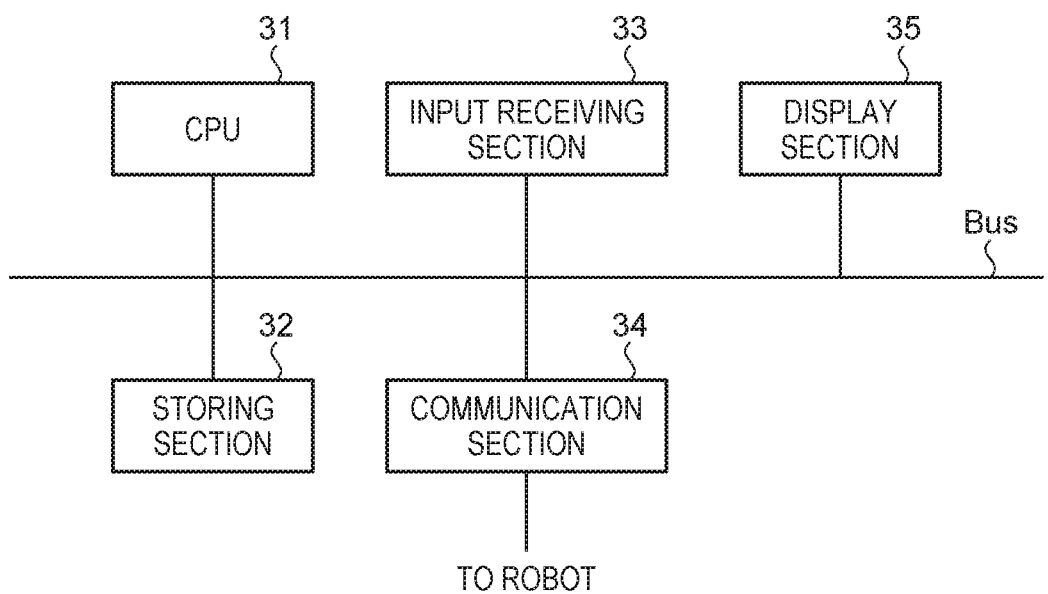
FIG. 2 is a diagram showing an example of a hardware configuration of a control device.

The hardware configuration of the control device 30 is explained with reference to FIG. 2. FIG. 2 is a diagram showing an example of the hardware configuration of the control device 30. The control device 30 includes, for example, a CPU (Central Processing Unit) 31, a storing section 32, an input receiving section 33, a communication section 34, and a display section 35. The control device 30 performs communication with the robot 20 via the communication section 34. The components are communicably connected to one another via a bus Bus.

The CPU 31 executes various computer programs stored in the storing section 32.

The storing section 32 includes, for example, a HDD (Hard Disk Drive) or an SSD (Solid State Drive), an EEPROM (Electrically Erasable Programmable Read-Only Memory), a ROM (Read-Only Memory), or a RAM (Random Access Memory). The storing section 32 stores various kinds of information and images to be processed by the control device 30, computer programs, the information indicating the position of the material supply region A, and the like. Note that, instead of a storage device incorporated in the control device 30, the storing section 32 may be an external storage device connected by a digital input/output port such as a USB.

The input receiving section 33 is a teaching pendant including, for example, a keyboard, a mouse, and a touchpad or another input device. Note that the input receiving section 33 may be configured integrally with the display section 35 as a touch panel.

The communication section 34 includes, for example, a digital input/output port such as a USB and an Ethernet (registered trademark) port.

The display section 35 is, for example, a liquid crystal display panel or an organic EL (Electroluminescence) display panel.

Figure 3:
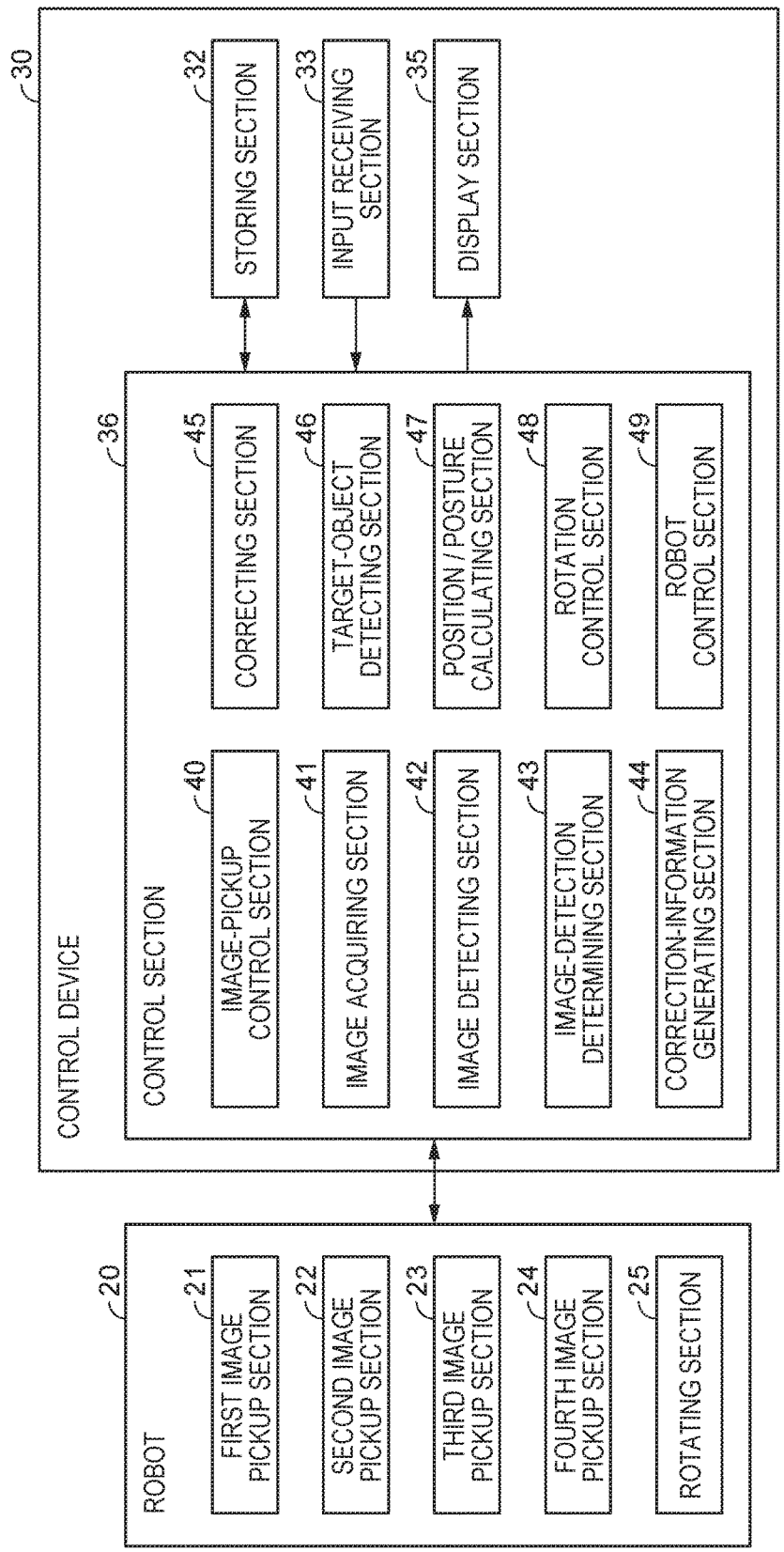
FIG. 3 is a diagram showing an example of a functional configuration of the control device.

The functional configuration of the control device 30 is explained with reference to FIG. 3. FIG. 3 is a diagram showing an example of the functional configuration of the control device 30. The control device 30 includes the storing section 32, an input receiving section 33, a display section 35, and a control section 36.

The control section 36 controls the entire control device 30. The control section 36 includes an image-pickup control section 40, an image acquiring section 41, an image detecting section 42, an image-detection determining section 43, a correction-information generating section 44, a correcting section 45, a target-object detecting section 46, a position/posture calculating section 47, a rotation control section 48, and a robot control section 49.

A part or all of the functional sections included in the control section 36 are realized by, for example, the CPU 31 executing various computer programs stored in the storing section 32. A part or all of the functional sections may be hardware function sections such as an LSI (Large Scale Integration) and an ASIC (Application Specific Integrated Circuit).

The image-pickup control section 40 causes a part or all of the first image pickup section 21, the second image pickup section 22, the third image pickup section 23, and the fourth image pickup section 24 to pick up ranges in which the respective image pickup sections can pick up images. When the extra-region image pickup section is set, the image-pickup control section 40 causes the extra-region image pickup section to pick up an image of the image pickup possible range. When the intra-region image pickup section is set, the image-pickup control section 40 causes the intra-region image pickup section to pick up an image of the image pickup possible range.

The image acquiring section 41 acquires the picked-up image picked up by the first image pickup section 21 from the first image pickup section 21. The image acquiring section 41 acquires the picked-up image picked up by the second image pickup section 22 from the second image pickup section 22. The image acquiring section 41 acquires the picked-up image picked up by the third image pickup section 23 from the third image pickup section 23. The image acquiring section 41 acquires the picked-up image picked up by the fourth image pickup section 24 from the fourth image pickup section 24. When the extra-region image pickup section is set, the image acquiring section 41 acquires the picked-up image picked up by the extra-region image pickup section from the extra-region image pickup section. When the intra-region image pickup section is set, the image acquiring section 41 acquires the picked-up image picked up by the intra-region image pickup section from the intra-region image pickup section. The image acquiring section 41 acquires the reference image stored in the storing section 32.

The image detecting section 42 detects a predetermined image included in the picked-up image acquired by the image acquiring section 41 as the target image. In this example, the predetermined image is the image of the marker P1 included in the target image. Note that the predetermined image may be an image of a marker provided in the target object O, the work table TB, or the like or an image of a part of the robot 20. The part of the robot 20 indicates a part serving for the marker P1, which is a characteristic part of the robot 20. The predetermined image may be another image detectable from the second picked-up image acquired by the image acquiring section 41. The image detecting section 42 detects the predetermined image from the target image through pattern matching or the like. The image detecting section 42 detects the predetermined image included in the reference image acquired by the image acquiring section 41.

The image-detection determining section 43 determines whether the image detecting section 42 detects the predetermined image from the reference image acquired by the image acquiring section 41. Note that the image-detection determining section 43 may further determine whether the image detecting section 42 detects the predetermined image from the picked-up image acquired by the image acquiring section 41 as the target image.

The correction-information generating section 44 generates the first correction information on the basis of the picked-up image acquired by the image acquiring section 41 as the target image and the reference image acquired by the image acquiring section 41. The correction-information generating section 44 stores the generated first correction information in the storing section 32. Note that, in this example, the second correction information is stored in the storing section 32 in advance. However, instead, the correction-information generating section 44 may generate the second correction information.

The correcting section 45 acquires the first correction information from the storing section 32. The correcting section 45 performs, on the basis of the acquired first correction information, the first correction on the picked-up image acquired by the image acquiring section 41, which is the picked-up image of the image pickup space. For example, as explained above, the correcting section 45 performs the first correction on the picked-up image picked up via the cover C1. The correcting section 45 acquires the second correction information from the storing section 32. The correcting section 45 performs, on the basis of the acquired second correction information, the second correction on the picked-up image acquired by the image acquiring section 41, which is the picked-up image of the image pickup space. For example, as explained above, the correcting section 45 performs the second correction on the picked-up image picked up not via the cover C1.

The target-object detecting section 46 detects the target object O from the picked-up image subjected to the first correction and the second correction or the second correction by the correcting section 45. For example, the target-object detecting section 46 detects the contour of the target object O as the target object O from the picked-up image of the image pickup space.

The position/posture calculating section 47 calculates the position and the posture of the target object O detected by the target-object detecting section 46. Note that the position/posture calculating section 47 calculates, for example, the position and the posture of the center of gravity of the target object O detected by the target-object detecting section 46.

When the image-detection determining section 43 determines that the image detecting section 42 does not detect the predetermined image from the picked-up image acquired as the target image from one or both of the third image pickup section 23 and the fourth image pickup section 24 by the image acquiring section 41, the rotation control section 48 causes the rotating section 25 to operate to thereby change the range in which the image pickup by the third image pickup section 23 and the fourth image pickup section 24 is possible.

The robot control section 49 causes the first arm and the second arm of the robot 20 to operate.

Processing in which the control section 36 causes the robot 20 to perform the predetermined work is explained below. In the following explanation, a specific example in which the first correction is performed on a picked-up image and a specific example in which the first correction is not performed on the picked-up image are separately explained.

Specific Example 1 in which the First Correction is Performed on a Picked-Up Image In a specific example 1 in which the first correction is performed on a picked-up image, the control device 30 causes the third image pickup section 23 to pick up an image of the image pickup space. Note that the control device 30 may be configured to cause the fourth image pickup section 24 to pick up an image of the image pickup space or may be configured to cause both of the third image pickup section 23 and the fourth image pickup section 24 to pick up stereo images of the image pickup space. In this case, as explained above, the third image pickup section 23 picks up an image of the image pickup space via the cover C1. Therefore, the control section 36 of the control device 30 generates the first correction information in order to perform the first correction on the picked-up image of the image pickup space.

Figure 4:
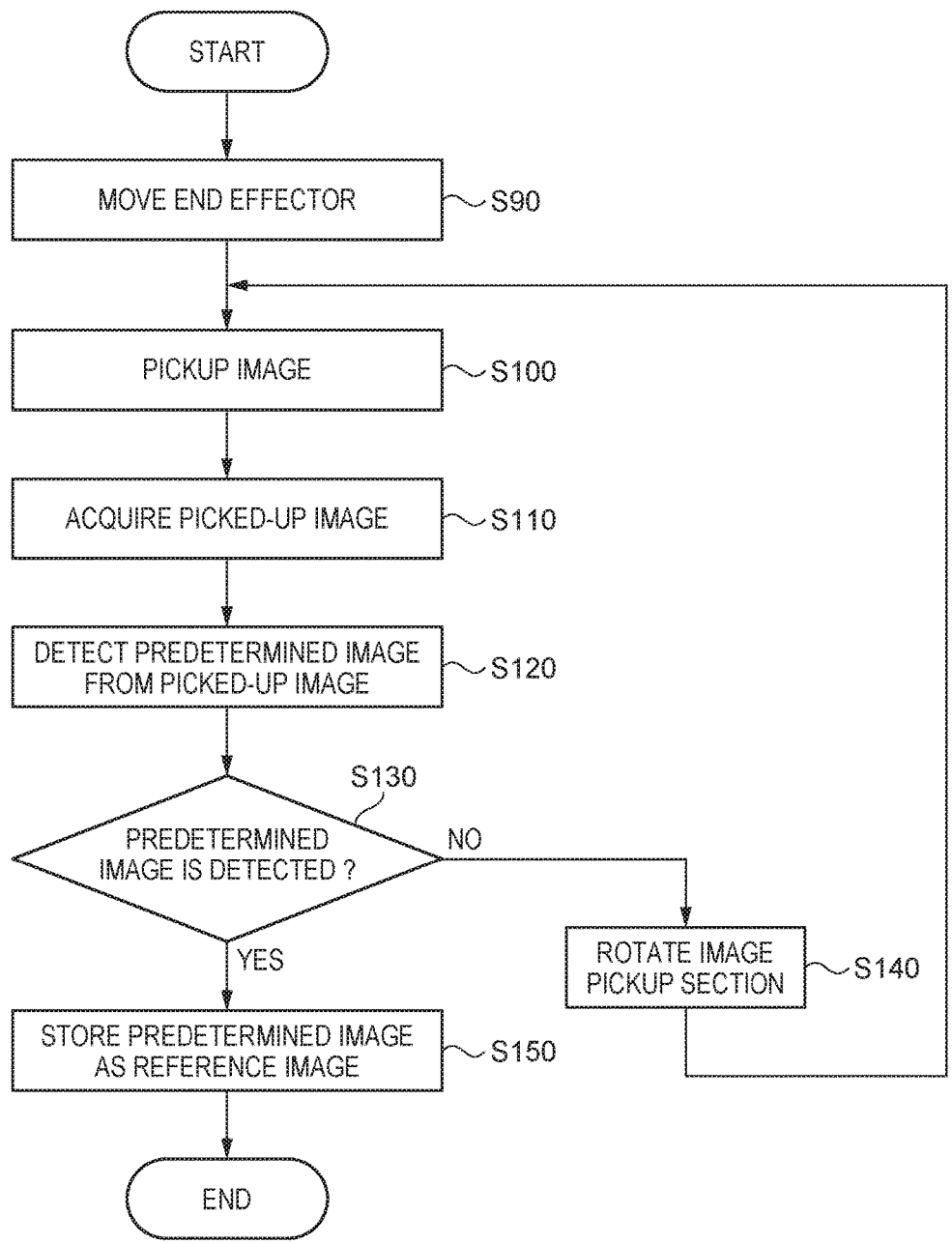
FIG. 4 is a flowchart for explaining an example of a flow of processing in which a control section acquires a reference image for generating first correction information.

Processing in which the control section 36 generates the first correction information is explained below with reference to FIGS. 4 to 7. FIG. 4 is a flowchart for explaining an example of a flow of processing in which the control section acquires the reference image for generating the first correction information. Note that, in the flowchart of FIG. 4, the cover C1 is detached from the clean bench C. In the following explanation, information indicating the position of the opening section of the cover C1 is stored in the storing section 32 in advance.

The robot control section 49 moves the first end effector E1 provided with the marker P1 into the work space S of the clean bench C from which the cover C1 is detached. The robot control section 49 sets the position and the posture of the moved first end effector E1 to, for example, a position and a posture in which the surface of the marker P1 is directed vertically update in the work space S. The robot control section 49 fixes the position and the posture of the first end effector E1 not to move (step S90). The direction of the surface of the marker P1 refers to, of directions of a Z axis at the time when an X axis and a Y axis indicating positions on the surface of the marker P1 are defined, a direction of a surface of the marker P1 not in contact the first end effector E1. Note that, in the following explanation, the position and the posture of the first end effector E1 fixed in step S90 are referred to as fixed position and posture.

In step S90, the robot control section 49 specifies a position where the opening section is present when the cover C1 is attached. The robot control section 49 causes the first end effector E1 to enter the work space S through the specified position. This is for the purpose of matching the position and the posture of the first end effector E1 with the fixed position and posture when the robot control section 49 causes the first end effector E1 to enter the work space S of the clean bench C attached with the cover C1 through the opening section according to the processing in the flowchart of FIG. 6. Note that, in step S90, the robot control section 49 specifies the position of the opening section by acquiring the information indicating the position of the opening section of the cover C1 from the storing section 32.

Subsequently, the image-pickup control section 40 causes the third image pickup section 23 to pick up an image of the range in which the image pickup by the third image pickup section 23 is possible (step S100). The image acquiring section 41 acquires the picked-up image from the third image pickup section 23 (step S110). The image detecting section 42 detects the predetermined image from the picked-up image acquired by the image acquiring section 41 in step S110 (step S120). As explained above, in this example, the predetermined image is the image of the marker P1. More specifically, the image of the marker P1 is an image of a portion where the image of the marker P1 provided in the first end effector E1 is picked up in the picked-up image.

Subsequently, the image-detection determining section 43 determines whether the image detecting section 42 has been able to detect the predetermined image from the picked-up image in step S120 (step S130). If the image-detection determining section 43 determines that the image detecting section 42 has not been able to detect the predetermined image from the picked-up image (No in step S130), the rotation control section 48 executes processing in step S140. On the other hand, when the image-detection determining section 43 determines that the image detecting section 42 has been able to detect the predetermined image from the picked-up image (Yes in step S130), the image detecting section 42 executes processing in step S150. In the following explanation, the processing in step S140 and subsequent steps is explained first.

If the image-detection determining section 43 determines that the image detecting section 42 has not been able to detect the predetermined image from the picked-up image, the rotation control section 48 rotates the rotating section 25 in a predetermined rotating direction by a predetermined angle (step S140). After the processing in step S140 is executed, the image-pickup control section 40 returns to step S100 and causes the third image pickup section 23 to pick up again an image of the range in which the image pickup by the third image pickup section 23 is possible. The predetermined rotating direction is, for example, a rotating direction in which the optical axes of the third image pickup section 23 and the fourth image pickup section 24, which rotate together with the rotating section 25, approach the vertical downward direction.

Note that, instead, the predetermined rotating direction may be a rotating direction opposite to the rotating direction in which the optical axes of the third image pickup section 23 and the fourth image pickup section 24 approach the vertical downward direction. When the rotating section 25 has rotated to a limit rotation angle for enabling the rotating section 25 to rotate in the predetermined rotating direction, the rotation control section 48 rotates the rotating section 25 in the rotating direction opposite to the rotating direction in which the optical axes of the third image pickup section and the fourth image pickup section 24 approach the vertically downward direction. The predetermined angle is, for example, 10°. Note that the predetermined angle may be another angle such as 5° or 15°.

Figure 5:
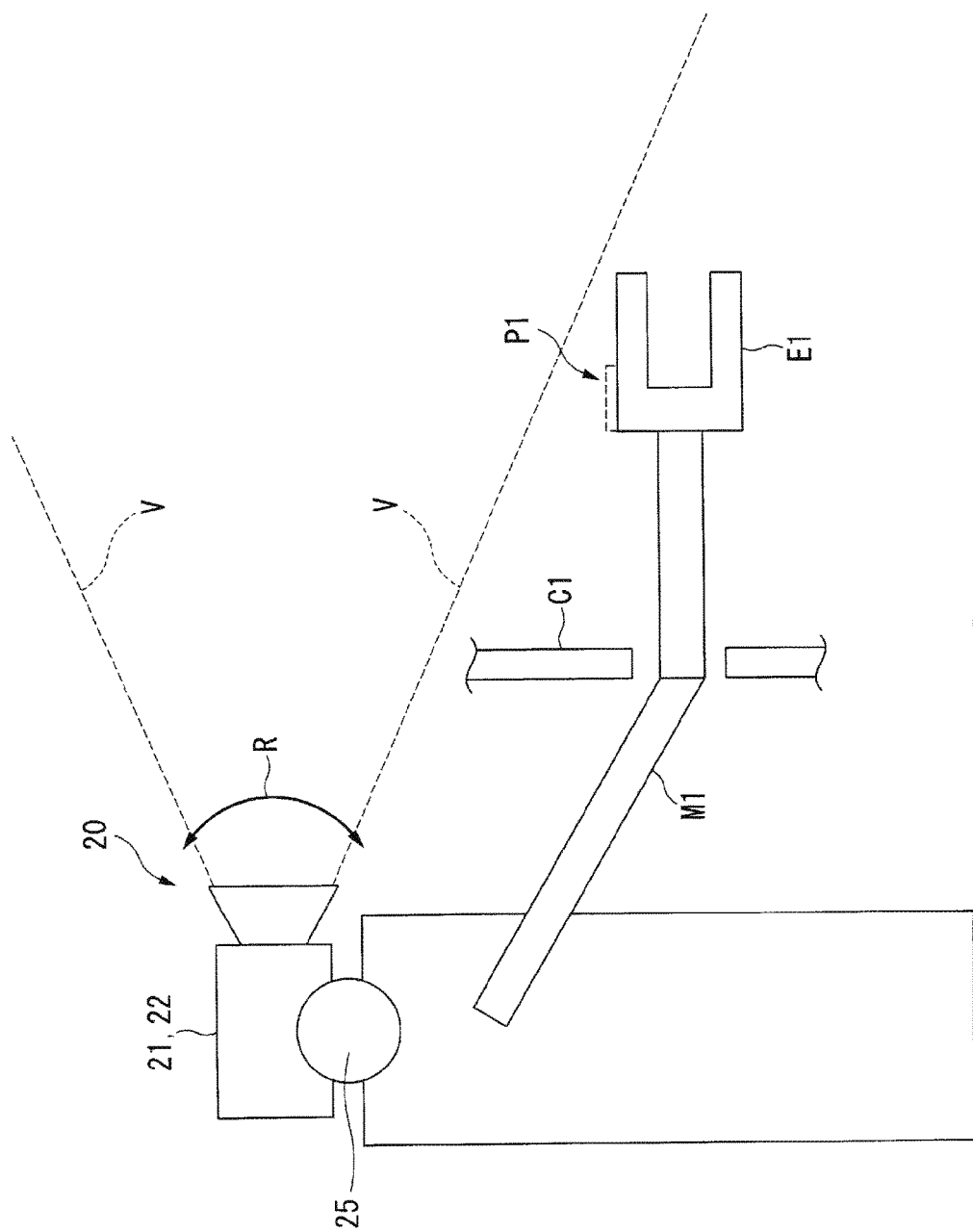
FIG. 5 is a diagram showing an example of a state in which a rotation control section rotates a rotating section.

The processing in step S140 is explained with reference to FIG. 5. FIG. 5 is a diagram showing an example of a state in which the rotation control section 48 rotates the rotating section 25. Note that, to simplify the figure, the exterior of the robot 20 shown in FIG. 5 is shown as an exterior different from the exterior of the robot 20 shown in FIG. 1.

The rotation control section 48 can rotate the optical axes of the third image pickup section 23 and the fourth image pickup section 24 in a direction along an arrow R by rotating the rotating section 25. A range between dotted lines V shown in FIG. 5 indicates the range (a range of an angle of view) in which the image pickup by the third image pickup section 23 and the fourth image pickup section 24 is possible.

As shown in FIG. 5, when the marker P1 provided in the first end effector E1 is not included in the range of the angle of view, the rotation control section 48 rotates the rotating section 25 in step S140 to thereby rotate the direction of the optical axis of the third image pickup section 23. Consequently, the range included in the angle of view of the third image pickup section 23, that is, the image pickup possible range changes. In the flowchart of FIG. 4, even when the predetermined image is not included in the picked-up image picked up by the third image pickup section 23, the control section 36 can cause the third image pickup section 23 to pick up an image of the range including the marker P1 provided in the first end effector E1 by repeating steps S100 to S140. In the following explanation, the range in which the third image pickup section 23 picks up the picked-up image in which the predetermined image is detected in step S130 is referred to as reference image pickup range.

Note that the robot 20 may not include a rotating mechanism. In this case, the third image pickup section 23 and the fourth image pickup section 24 are set in positions where image pickup of the reference image pickup range is possible. In this case, in the flowchart of FIG. 4, the processing in steps S130 and S140 is omitted.

In the following explanation, processing in step S150 and subsequent steps is explained. When determining that the image detecting section 42 has been able to detect the predetermined image from the picked-up image, the image-detection determining section 43 specifies the picked-up image as the reference image. The image-detection determining section 43 stores the specified reference image in the storing section 32 (step S150). The image-detection determining section 43 stores, in the storing section 32, information indicating a rotation angle of the rotating section 25 at the time when the picked-up image specified as the reference image in step S150 is picked up.

The control section 36 acquires the reference image as explained above. Note that the reference image may be a CG (Computer Graphics) simulating an image obtained by picking up an image of the reference image pickup range including the marker P1 not via the cover C1. In this case, the control section 36 omits the processing of the flowchart of FIG. 4.

Figure 6:
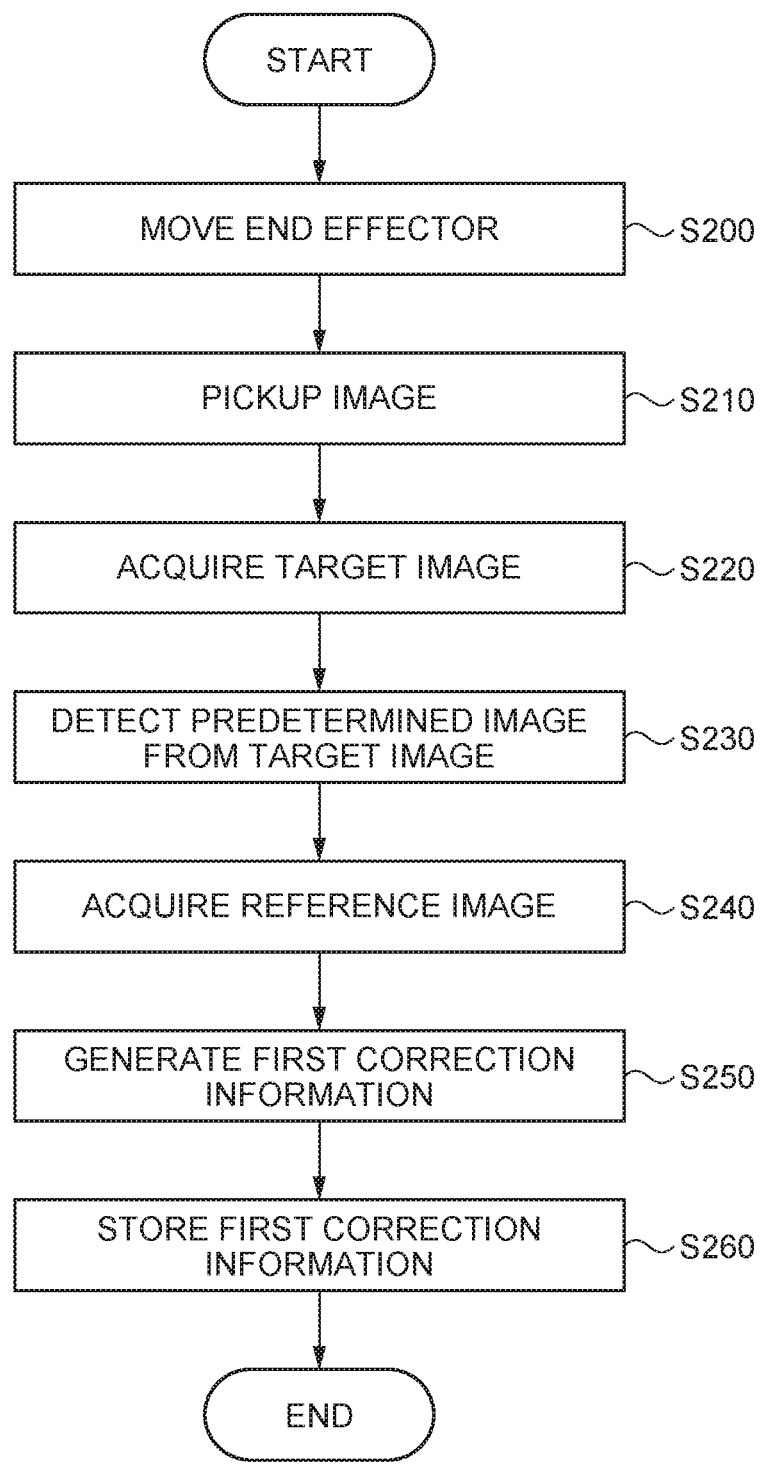
FIG. 6 is a flowchart for explaining an example of a flow of processing in which the control section acquires a target image and generates the first correction information.

FIG. 6 is a flowchart for explaining an example of a flow of processing in which the control section 36 acquires the target image and generates the first correction information. Note that the processing of the flowchart of FIG. 6 is processing executed by the control section 36 in a state in which the cover C1 is attached to the clean bench C after the processing of the flowchart of FIG. 4 is executed by the control section 36. In the following explanation, the information indicating the position of the opening section of the cover C1 is stored in the storing section 32 in advance.

The robot control section 49 acquires the information indicating the position of the opening section of the cover C1 from the storing section 32. Note that, since the information indicating the position of the opening section is already acquired from the storing section 32 in step S90 shown in FIG. 4, the robot control section 49 may omit the processing for acquiring the information indicating the position of the opening section from the storing section 32. The robot control section 49 causes the first end effector E1 to enter the work space S through the opening section of the cover C1. The robot control section 49 matches the position and the posture of the first end effector E1 in the work space S with the fixed position and posture (step S200).

Subsequently, the rotation control section 48 acquires, from the storing section 32, the information indicating the rotation angle of the rotating section 25 at the time when the picked-up image specified as the reference image in step S150 is picked up. The rotation control section 48 matches, on the basis of the acquired information indicating the rotation angle, the rotation angle of the rotating section 25 with the rotation angle of the rotating section 25 at the time when the picked-up image specified as the reference image in step S150 is picked up. Consequently, the range in which the image pickup by the third image pickup section 23 is possible coincides with the reference image pickup range. The image-pickup control section 40 causes the third image pickup section 23 to pick up an image of the reference image pickup range (step S210).

Subsequently, the image acquiring section 41 acquires, as the target image, the picked-up image picked up by the third image pickup section 23 in step S210 (step S220). The image detecting section 42 detects the predetermined image from the target image acquired by the image acquiring section 41 in step S220 (step S230). The image acquiring section 41 acquires the reference image from the storing section 32 (step S240).

Subsequently, the correction-information generating section 44 generates the first correction information on the basis of the target image in which the predetermined image is detected by the image detecting section 42 in step S230 and the reference image acquired by the image acquiring section 41 in step S240 (step S250). Generation processing of the first correction information performed by the correction-information generating section 44 in step S250 is explained with reference to FIGS. 7A to 7C. FIGS. 7A to 7C are diagrams showing an example of the target image in which the predetermined image is detected by the image detecting section 42 in step S230 and an example of the reference image acquired by the image acquiring section 41 in step S240.

In FIG. 7A, a target image G1, which is an example of the target image in which the predetermined image is detected by the image detecting section 42 in step S230, is shown. In FIG. 7B, a reference image G2, which is an example of the reference image acquired by the image acquiring section 41 in step S240, is shown. In FIG. 7C, an image G3 obtained by superimposing the target image G1 and the reference image G2 such that a frame of the target image G1 and a frame of the reference image G2 coincide with each other is shown.

As shown in FIG. 7A, the target image G1 includes an image CP1 of the marker P1 as the predetermined image. As shown in FIG. 7B, the reference image G2 includes an image CP2 of the marker P1 as the predetermined image. As shown in FIG. 7C, when the target image G1 and the reference image G2 are superimposed such that the frame of the target image G1 and the frame of the reference image G2 coincide with each other, the position of the image CP1 and the position of the image CP2 in the superimposed image G3 do not coincide with each other.

This is a result of a shift of the position of the image CP1 included in the target image G1 due to distortion caused because the image pickup is performed via the cover C1 when the third image pickup section 23 picks up an image of the reference image pickup range including the marker P1. In order to correct the distortion, the correction-information generating section 44 calculates a difference (an offset) between the position and the posture of the image CP1 included in the target image G1 and the position and the posture of the image CP2 included in the reference image G2. The correction-information generating section 44 generates, as the first correction information, a correspondence table that associates coordinates indicating positions represented by pixels of the target image G1 and coordinates obtained by shifting, by the calculated difference, the coordinates indicating the positions represented by the pixels of the target image G1.

Note that, instead of the correspondence table, the first correction information may be other information as long as the information associates the coordinates indicating the positions represented by the pixels of the target image G1 and the coordinates obtained by shifting, by the calculated difference, the coordinates indicating the positions represented by the pixels of the target image G1. The correction-information generating section 44 may be configured to calculate the offset and stores the calculated offset as the first correction information. In this case, in performing the first correction on the picked-up image on the basis of the first correction information, the correcting section 45 performs the first correction by translating the coordinates indicating the positions represented by the pixels of the picked-up image by an amount of the offset, which is the first correction information.

After generating the first correction information in step S250, the correction-information generating section 44 stores the generated first correction information in the storing section 32 (step S260).

As explained above, the control section 36 generates the first correction information on the basis of the target image and the reference image. Note that it is unnecessary to repeatedly perform the processing of the flowcharts of FIGS. 4 and 6 every time predetermined work is performed unless the material, the thickness, and the like of the cover C1 attached to the clean bench C are changed. Consequently, the control section 36 can improve efficiency of work. Note that, instead, the generation processing may be repeatedly performed every time the predetermined work is performed.

Figure 8:
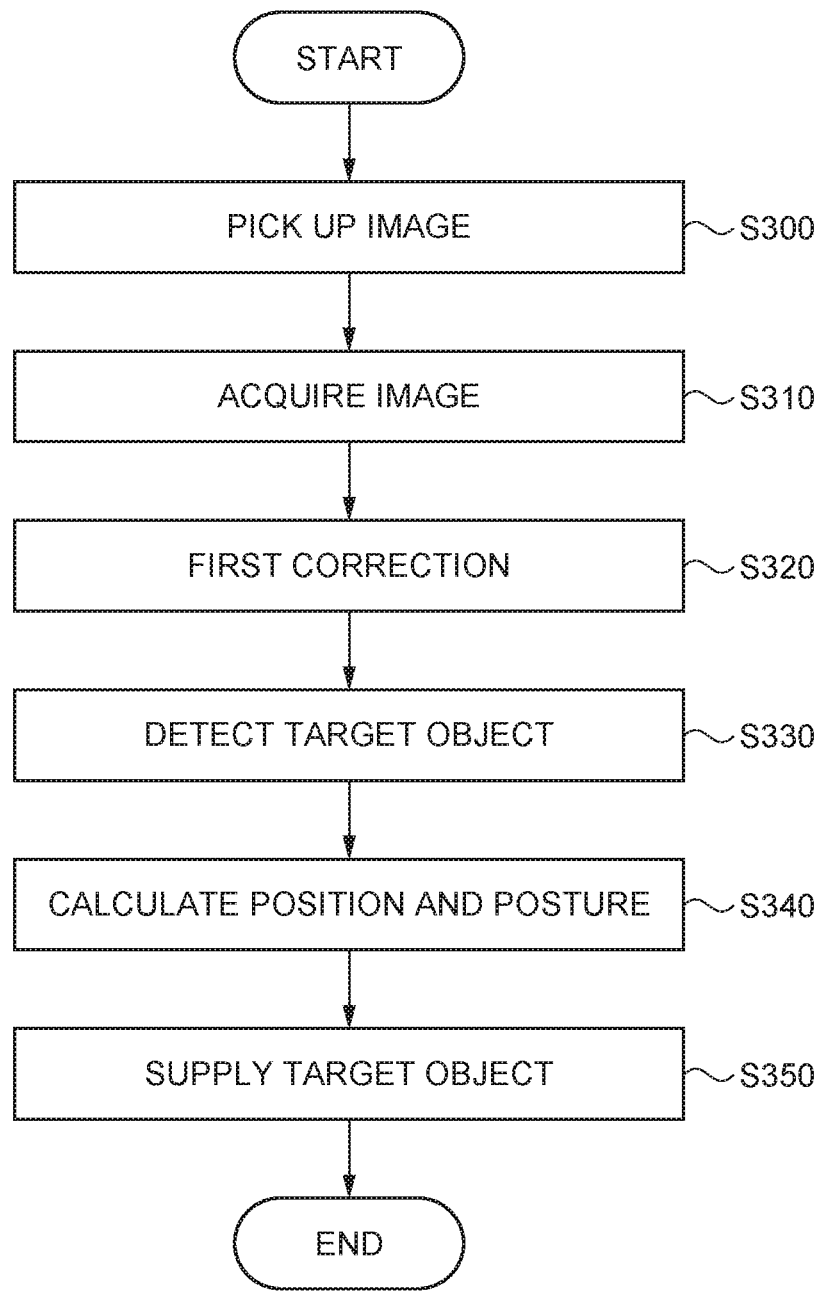
FIG. 8 is a flowchart for explaining an example of a flow of processing in which the control section performs first correction on the basis of the first correction information and causes the robot to perform predetermined work.

Processing in which the control section 36 performs the first correction on the basis of the first correction information and causes the robot 20 to perform the predetermined work is explained with reference to FIG. 8. FIG. 8 is a flowchart for explaining an example of a flow of the processing in which the control section 36 performs the first correction on the basis of the first correction information and causes the robot 20 to perform the predetermined work. Note that, in the flowchart of FIG. 8, the cover C1 is attached to the clean bench C. In the flowchart of FIG. 8, a range including the target object O, that is, the image pickup space is already included in the range of the angle of view of the third image pickup section 23. In the following explanation, explanation is omitted concerning the second correction performed on the picked-up image by the correcting section 45. For example, the correcting section 45 may be configured to perform the second correction before and after the first correction or perform the second correction in parallel to the first correction in step S320.

The image-pickup control section 40 causes the third image pickup section 23 to pick up an image of the image pickup space (step S300). Subsequently, the image acquiring section 41 acquires, from the third image pickup section 23, the picked-up image picked up by the third image pickup section 23 in step S300 (step S310). The correcting section 45 acquires the first correction information from the storing section 32. The correcting section 45 performs, on the basis of the acquired first correction information, the first correction on the picked-up image acquired by the image acquiring section 41 in step S310 (step S320). That is, the correcting section 45 converts, on the basis of the first correction information, coordinates indicating positions representing pixels of the picked-up image into coordinates associated with the coordinates in the first correction information.

Subsequently, the image detecting section 42 detects the target object O from the picked-up image subjected to the first correction in step S320 (step S330). The position/posture calculating section 47 calculates the position and the posture of the target object O detected by the image detecting section 42 in step S330 (step S340). The robot control section 49 acquires the information indicating the position of the material supply region A from the storing section 32. The robot control section 49 causes the first end effector E1 to grasp the target object O on the basis of the position and the posture of the target object O calculated by the position/posture calculating section 47 in step S340. The robot control section 49 moves the first end effector E1 on the basis of the acquired information indicating the position of the material supply region A to thereby supply the target object O gripped by the first end effector E1 to the material supply region A (step S350).

As explained above, the control section 36 performs the first correction on the picked-up image of the image pickup space picked up by the third image pickup section 23 and causes the robot 20 to operate on the basis of the picked-up image subjected to the first correction to thereby cause the robot 20 to perform a predetermined operation. Consequently, the control section 36 can improve efficiency and accuracy of work. In particular, since the control section 36 calculates the position and the posture of the target object O on the basis of the picked-up image picked up by the third image pickup section 23, the position and the posture of the target object O does not need to be arranged in a position and a posture determined in advance on the work table TB. As a result, even if a special device is not prepared, it is possible to replace an operator who performs work using the clean bench C with the robot 20.

Specific Example 2 in which the First Correction is Performed on a Picked-Up Image In a specific example 2 in which the first correction is performed on a picked-up image, the control device 30 causes one or both of the first image pickup section 21 and the second image pickup section 22 to pick up an image of the image pickup space. More specifically, the robot control section 49 moves one or both of the first arm and the second arm to thereby cause one or both of the first image pickup section 21 and the second image pickup section 22 to perform the processing in step S100 of the flowchart of FIG. 4 and the processing in step S210 of the flowchart of FIG. 6. Consequently, the control section 36 can obtain effects same as the effects of the specific example 1 in which the first correction is performed on the picked-up image.

Specific Example 3 in which the First Correction is Performed on a Picked-Up Image In a specific example 3 in which the first correction is performed on a picked-up image, the control device 30 causes the extra-region image pickup section to pick up an image of the image pickup space. More specifically, the image-pickup control section 40 causes the extra-region image pickup section to pick up an image of the image pickup possible range to thereby cause the extra-region image pickup section to perform the processing in step S100 of the flowchart of FIG. 4 and the processing in step S210 of the flowchart of FIG. 6. Consequently, the control section 36 can obtain effects same as the effects of the specific example 1 in which the first correction is performed on the picked-up image.

Specific Example 1 in which the First Correction is not Performed on a Picked-Up Image In a specific example 1 in which the first correction is not performed on a picked-up image, in a state in which the cover C1 is attached to the clean bench C, the control device 30 causes the first image pickup section 21 to enter the inner side of the cover C1 and causes the first image pickup section 21 in the cover C1 to pick up an image of the image pickup space. Note that the control device 30 may be configured to cause the second image pickup section 22 to pick up an image of the image pickup space.

Figure 9:
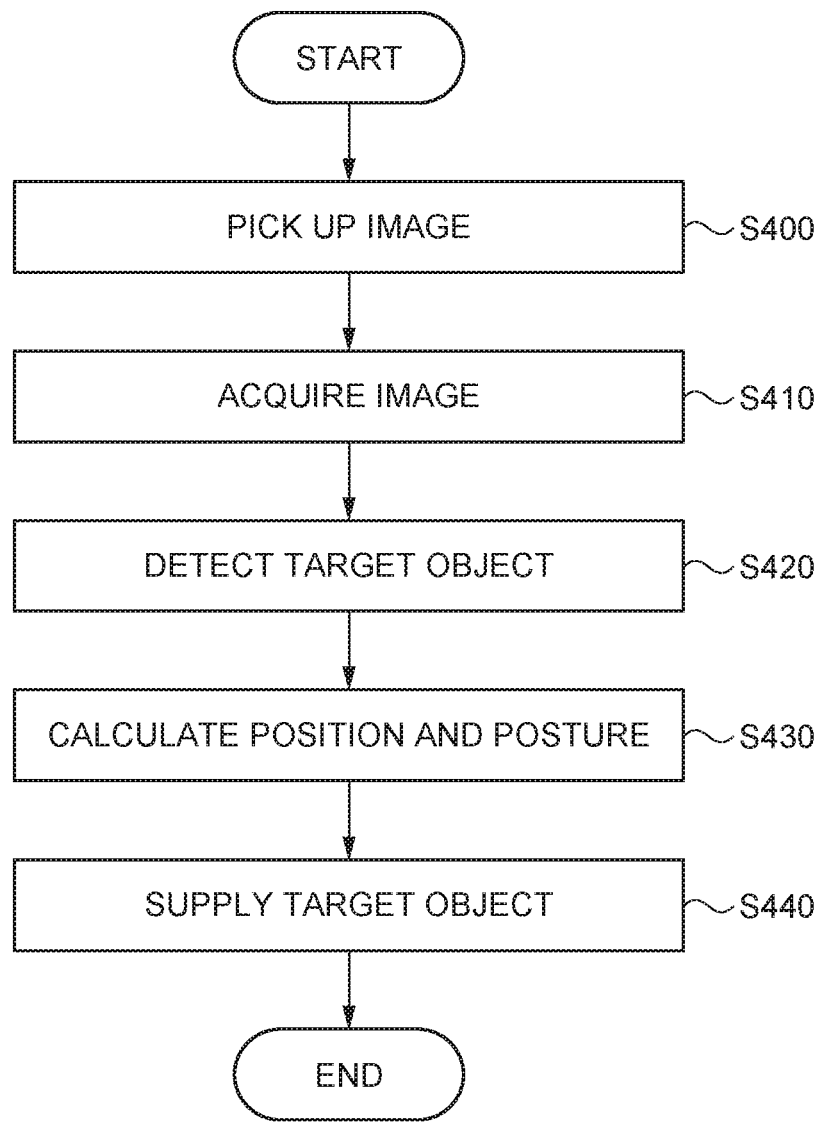
FIG. 9 is a flowchart for explaining an example of a flow of processing in which the control section causes the robot to perform the predetermined work in a specific example 1 in which the control section does not perform the first correction on a picked-up image.

In the specific example 1, the processing of the flowcharts of FIGS. 4 and 6 is not performed. Processing in which the control section 36 causes the robot 20 to perform the predetermined work in the specific example 1 in which the first correction is not performed on a picked-up image is explained with reference to FIG. 9. FIG. 9 is a diagram showing an example of a flow of the processing in which the control section 36 causes the robot 20 to perform the predetermined work in the specific example 1 in which the first correction is not performed on a picked-up image. Note that, in the following explanation, explanation is omitted concerning second correction performed on a picked-up image by the correcting section 45. For example, the correcting section 45 performs the second correction before the target object O is detected from the picked-up image in step S420.

The robot control section 49 acquires the information indicating the position of the opening section of the cover C1 from the storing section 32. The robot control section 49 causes the first end effector E1 to enter the work space S through the opening section of the cover C1 on the basis of the acquired information indicating the position of the opening section. The robot control section 49 sets the position and the posture of the first end effector E1 in the work space S to a position and a posture in which the image pickup possible range of the first image pickup section 21 coincides with the image pickup space. The robot control section 49 fixes the position and the posture of the first end effector E1 not to move (step S400).

Subsequently, the image acquiring section 41 acquires, from the first image pickup section 21, the picked-up image picked up by the first image pickup section 21 in step S400 (step S410). The image detecting section 42 detects the target object O from the picked-up image acquired by the image acquiring section 41 in step S410 (step S420). The position/posture calculating section 47 calculates the position and the posture of the target object O detected by the image detecting section 42 in step S420 (step S430).

Subsequently, the robot control section 49 acquires the information indicating the position of the material supply region A from the storing section 32. The robot control section 49 causes the first end effector E1 to grip the target object O on the basis of the position and the posture of the target object O calculated by the position/posture calculating section 47 in step S430. The robot control section 49 moves the first end effector E1 on the basis of the acquired information indicating the position of the material supply region A to thereby supply the target object O gripped by the first end effector E1 to the material supply region A (step S440).

As explained above, the control section 36 operates on the basis of the picked-up image of the work space S, between which and the robot 20 the cover C1 functioning as the transparent member G is disposed, picked up by the first image pickup section 21. The control section 36 causes the robot 20 to perform the predetermined work. Consequently, the control section 36 can improve efficiency of work.

Specific Example 2 in which the First Correction is not Performed on a Picked-Up Image In a specific example 2 in which the first correction is not performed on a picked-up image, the control device 30 causes the intra-region image pickup section to pick up an image of the image pickup space. More specifically, the image-pickup control section 40 causes the intra-region image pickup section to pick up an image of the image pickup possible range to thereby cause the intra-region image pickup section to perform the processing in step S400 of the flowchart of FIG. 9. Consequently, the control section 36 can obtain effects same as the effects of the specific example 1 in which the first correction is not performed on the picked-up image.

As explained above, in the robot 20 in this embodiment, the transparent member G is disposed between the robot 20 and the work space S of the robot 20. At least a part of the work space S of the robot 20 operates on the basis of the picked-up image picked up by a part or all of the four image pickup sections included in the robot 20, the extra-region image pickup section, or the intra-region image pickup section. Consequently, the robot 20 can improve efficiency of work. For example, the robot 20 can improve efficiency and accuracy of work in the work space S surrounded by the transparent member G like the clean bench C. In the following explanation, when the image pickup section is simply referred to, the image pickup section indicates any one of a part or all of the four image pickup sections included in the robot 20, the extra-region image pickup section, and the intra-region image pickup section.

The robot 20 operates on the basis of the picked-up image picked up by a part or all of the four image pickup sections included in the robot 20. Consequently, the robot 20 can improve efficiency and accuracy of work using a part or all of the four image pickup sections included in the robot 20.

The robot 20 picks up an image of at least a part of the work space S with one or both of the first image pickup section 21 and the second image pickup section 22 moved into the work space S. Consequently, the robot 20 can improve efficiency and accuracy of work using one or both of the first image pickup section 21 and the second image pickup section 22 moved into the work space S.

The robot 20 operates on the basis of the picked-up image of at least a part of the work space S picked up by the image pickup section via the transparent member G and the reference image. Consequently, the robot 20 can improve efficiency and accuracy of work using the image pickup section that picks up an image of the work space S via the transparent member G.

The robot 20 operates on the basis of the target image, which is the picked-up image including the predetermined image picked up via the transparent member G, and the reference image including the predetermined image picked up by the image pickup section not via the transparent member G. Consequently, the robot 20 can improve efficiency and accuracy of work on the basis of the picked-up image including the predetermined image and the reference image including the predetermined image.

The robot 20 operates on the basis of the target image, which is the picked-up image picked up via the transparent member G and including the image of the marker, and the reference image picked up by the image pickup section not via the transparent member G and including the image of the marker. Consequently, the robot 20 can improve efficiency and accuracy of work on the basis of the target image including the image of the marker and the reference image including the image of the marker.

The robot 20 operates on the basis of the target image picked up via the transparent member G and including the image of a part of the robot 20 and the reference image picked up by the image pickup section not via the transparent member G and including the image of apart of the robot 20. Consequently, the robot 20 can improve efficiency and accuracy of work on the basis of the target image including the image of a part of the robot 20 and the reference image including the image of a part of the robot 20.

The robot 20 operates on the basis of the picked-up image picked up by the extra-region image pickup section provided outside the work space S. Consequently, the robot 20 can improve efficiency and accuracy of work using the extra-region image pickup section provided outside the work space S.

The robot 20 operates on the basis of the picked-up image picked up by the intra-region image pickup section provided in the work space S. Consequently, the robot 20 can improve efficiency and accuracy of work using the intra-region image pickup section provided in the work space S.

The embodiment of the invention is explained in detail above with reference to the drawings. However, a specific configuration is not limited to the embodiment and may be, for example, changed, substituted, or deleted without departing from the spirit of the invention.

A computer program for realizing the functions of any components in the device (e.g., the control device 30 of the robot 20) explained above may be recorded in a computer-readable recording medium and read and executed by a computer system. Note that the "computer system" includes an OS (Operating System) and hardware such as peripheral devices. The "computer-readable recording medium" refers to a portable medium such as a flexible disk, a magneto-optical disk, a ROM, or a CD (Compact Disk)-ROM or a storage device such as a hard disk incorporated in the computer system. Further, the "computer-readable recording medium" includes a recording medium that stores a computer program for a fixed time such as a volatile memory (a RAM) inside a computer system functioning as a server or a client when a computer program is transmitted via a network such as the Internet or a communication line such as a telephone line.

The computer program may be transmitted from a computer system, which stores the computer program in a storage device, to another computer system via a transmission medium or by a transmission wave in the transmission medium. The "transmission medium", which transmits the computer program, refers to a medium having a function of transmitting information such as a network (a communication network) such as the Internet or a communication line (a communication wire) such as a telephone line.

The computer program may be a computer program for realizing a part of the functions explained above. Further, the computer program may be a computer program that can realize the functions in a combination with a computer program already recorded in the computer system, a so-called differential file (a differential program).

The entire disclosure of Japanese Patent Application No. 2015-121782, filed Jun. 17, 2015 is expressly incorporated by reference herein.

What is claimed is:

1. A robot comprising:
an arm, the arm being configured to operate in a work space;
an image pickup device configured to obtain images of the work space, the images including first and second images;
a transparent member provided to cover the work space;
a memory configured to store computer-readable instructions; and
a processor configured to execute the computer-readable instructions so as to:
cause the image pickup device to obtain the first image when the transparent member exists between the image pickup device and the work space;
cause the image pickup device to obtain the second image when the transparent member is out of a space between the image pickup device and the work space;
generate correction information based on the first and second images; and
operate the arm based on the correction information,
wherein the processor is configured to obtain an image difference between the first and second images, and
the correction information is generated based on the image difference.

2. The robot according to claim 1,
wherein the arm has a marker thereon, and
each of the first and second images includes an image of the marker.

3. The robot according to claim 1,
wherein each of the first and second images includes an image of a part of the robot.

4. A control device controlling an image pickup device and a robot arm, the robot arm being operable in a work space, the control device comprising:
a memory configured to store computer-readable instructions; and
a processor configured to execute the computer-readable instructions so as to:
cause the image pickup device to obtain a first image when a transparent member exists between the image pickup device and the work space;
cause the image pickup device to obtain a second image when the transparent member is out of a space between the image pickup device and the work space;
generate correction information based on the first and second images; and
operate the robot arm based on the correction information
wherein the processor is configured to obtain an image difference between the first and second imaqes, and
the correction information is generated based on the image difference.

5. A control method for causing a processor to execute computer-readable instructions stored in a memory so as to control a robot arm configured to operate in a work space covered by a transparent member and an image pickup device configured to obtain images of the work space, the control method comprising executing in the processor the steps of:
causing the image pickup device to obtain a first image when the transparent member exists between the image pickup device and the work space;

causing the image pickup device to obtain a second image when the transparent member is out of a space between the image pickup device and the work space;
generating correction information based on the first and second images; and
operating the robot arm based on the correction information,
wherein the processor is configured to obtain an image difference between the first and second imaqes, and
the correction information is qenerated based on the imaqe difference.

6. The control device according to claim 4,
wherein the robot arm has a marker thereon, and
each of the first and second images includes an image of the marker.

7. The control device according to claim 4,
wherein each of the first and second images includes an image of a part of the robot arm.

8. The control method according to claim 5,
wherein the robot arm has a marker thereon, and
each of the first and second images includes an image of the marker.

9. The control method according to claim 5,
wherein each of the first and second images includes an image of a part of the robot arm.

* * * * *